United States Patent [19]

Kerlau et al.

[11] Patent Number: 5,814,743
[45] Date of Patent: Sep. 29, 1998

[54] DEVICE FOR TAKING SAMPLES OF NOXIOUS LIQUIDS, PARTICULARLY LIQUIDS CHARGED WITH SOLID PARTICLES

[75] Inventors: Daniel Kerlau, Chatenay Malabry; Thierry Prevost, Elancourt; Patrice Roux, Paris, all of France

[73] Assignee: Compagnie Generale Des Matieres Nucleaires, Velizy Villacoublay, France

[21] Appl. No.: 840,566

[22] Filed: Apr. 21, 1997

[30] Foreign Application Priority Data

Apr. 22, 1996 [FR] France .................................. 96 05011

[51] Int. Cl.⁶ ...................................................... G01N 1/14
[52] U.S. Cl. .......................................................... 73/863.83
[58] Field of Search ........................... 73/863.81, 863.83, 73/864.31, 864.34

[56] References Cited

U.S. PATENT DOCUMENTS

| | | |
|---|---|---|
| 4,106,155 | 8/1978 | Fosslien . |
| 4,118,987 | 10/1978 | Zeh . |
| 4,228,864 | 10/1980 | Berger et al. . |
| 4,516,436 | 5/1985 | Conche et al. . |
| 4,662,231 | 5/1987 | Schaarschmidt et al. . |
| 4,683,761 | 8/1987 | Stock .................................. 73/864.34 |
| 4,986,138 | 1/1991 | Spencer ............................... 73/864.34 |
| 4,991,450 | 2/1991 | Schaarschmidt et al. . |
| 5,038,623 | 8/1991 | Zeh . |
| 5,279,167 | 1/1994 | Peterson .............................. 73/864.34 |

FOREIGN PATENT DOCUMENTS

| | | |
|---|---|---|
| 0003936 | 9/1979 | European Pat. Off. . |
| 0078212 | 5/1983 | European Pat. Off. . |
| 2347671 | 11/1977 | France . |
| 2555746 | 5/1985 | France . |
| 2633395 | 12/1989 | France . |
| 2229422 | 9/1990 | United Kingdom . |

*Primary Examiner*—Robert Raevis
*Attorney, Agent, or Firm*—Pearne, Gordon, McCoy & Granger LLP

[57] ABSTRACT

A device for taking samples of noxious liquids, notably radioactive liquids. A protective enclosure (7) contains notably a circulation unit (10) in the form of a jet pump supplied by a driving arm (19). The liquid to be analysed is aspirated by an aspiration arm (17) and discharged with a drive liquid via a return arm (18). A sampling flask is pressed under a support plate (9) where the aspiration and return arms (17 and 18) emerge and closes the sampling circuit. This method is recommended above all for viscous liquids, liquid sludges and liquids charged with large size solid particles, since the sample only passes through pipes of an adequate diameter and is not subjected to any mixing or disturbance. A correct sampling is therefore ensured.

16 Claims, 5 Drawing Sheets

DEVICE FOR TAKING SAMPLES OF NOXIOUS LIQUIDS, PARTICULARLY LIQUIDS CHARGED WITH SOLID PARTICLES

BACKGROUND OF THE INVENTION

This invention relates to a device for taking samples of radioactive liquids or liquids which are noxious for another reason, particularly those charged with solid particles, and which can have any degree of turbidity or consistency from the least viscous liquids to slurries.

The taking of liquid samples is subject to particular constraints in the nuclear industries because of their dangerous character. Generally, the products to be analysed are, before sampling, in tanks, in which there are sampling pipes which pass through a protective wall and lead to an area assigned for the analysis. Air lifts are arranged in the drums to raise the liquids into the sampling pipes. The samples are then introduced into hermetically sealed flasks, called pitchers by the applicant. These pitchers are transferred via a pneumatic network to the analysis installations. The traditional filling method consists of piercing the stopper of the flasks, which is made of rubber, with a needle situated at the end of the sampling pipe, which dispenses with removal of the stopper : the sample is aspirated into the flask previously evacuated via the needle. But it is clear that this method is no longer suitable for viscous, heterogeneous samples or liquids charged with large particles because of the fineness of the needle.

However, the document FR-A-2 633 395 describes a device which has certain similarities to the invention; the flask to be filled has its stopper removed and is applied under a support plate under which sampling circuit pipes emerge which allow its gaseous contents to be emptied and permit it to be filled with liquid. But these pipes only form a diversion of the sampling circuit, which is continuous even when the flask is withdrawn, so that it is difficult to predict the quantity and the composition of the liquid that will take the diversion and remain in the flask, the filling of which can be problematic. The samples collected will, in any case be distorted by an air lift which remains present at the entry to the sampling circuit even if a pneumatic ejector is arranged in the circuit downstream from the flask, since this ejector does not ensure the circulation of the liquid but a small raising of the liquid in order to start the lift.

The main objective of the invention is therefore to satisfy the need to take samples that are properly representative of the mixture or the solid-liquid suspension from which they are extracted, whilst avoiding any alteration of its composition or of the size distribution of the particles and whilst avoiding also separation of the constituents, by using a sample taking device based on a completely different principle. This involves replacing the needle and the air lift by means that do not compromise safety and also the confining of the device, despite the opening for the flasks that becomes necessary.

SUMMARY OF THE INVENTION

This objective is achieved if the device for taking samples of noxious liquids includes a sampling circuit that includes an aspiration arm leading to the tank and a return arm, a unit for circulating liquid through the sampling circuit and a support plate under which the ends of the aspiration and return arms emerge, a rim of the flasks being applied under the support plate around said ends, characterized in that the aspiration and sampling arms have no communication other than via the flasks applied under the support plate, the liquid circulation unit is situated on the return arm and the aspiration arm is connected to a vent. The method then consists of aspirating the sampled product and causing it to pass along the sampling circuit, of which the flask is temporarily a part, when it is pressed against the lower surface of the support plate, by connecting together the arms of the sampling circuit which are cut off from one another when the flask is withdrawn. The aspiration is carried out for a sufficient time for the product contained in the flask to be representative of the contents of the tank from which it originates. This flask is then withdrawn and restoppered. The aspiration does not disturb nor significantly distort the product and the pipes have sufficient cross section for the largest particles not to be stopped. The cross section is optimised in order to obtain a circulation rate that is sufficient to prevent segregation within the circuits. The venting of the sampling circuit while the aspiration continues, allows emptying of the sampling circuit and avoids the dangers and the contamination of subsequent samples which would arise from any remaining aspirated liquid. The flask remains partially filled when the rest of the sampling circuit is emptied.

Another objective of the invention is to allow the taking of samples without danger for plant personnel. It is therefore recommended that one adds to the device, an enclosure equipped with access for the entry and the exit of the flasks, the sampling and aspiration arms and the support plate being situated within the enclosure, the sampling and aspiration arms being connected to aspiration and return pipes outside the enclosure and, arranged within the enclosure, means of grasping the flasks, means for the removal and the replacement of flask stoppers, and means of applying the flasks under the support plate, the vent including a pipe that ends within the enclosure and which has a part outside the enclosure fitted with a venting valve.

It is advantageous that the device be constructed in the form of a vehicle that is mobile over the ground thanks to wheels on which the enclosure is mounted, and that one may make a choice from the sampling pipes, whose ends pass through the protective wall, according to the test or the analysis that one wishes to carry out. The circulation unit can be a pump, however the use of a pump for aspirating the product can be a problem under the conditions particular to the invention, since the usual pumps, with moving mechanical components, would often be soiled or damaged by the impurities and it is not desirable to carry out pump changes which would involve an additional opening up of the enclosure and the appearance of a contaminated component on the outside. This is why the use of a jet pump is recommended for pumping ; the sampling circuit then includes a driving arm supplied by liquid under pressure and ending up in the return branch of the sampling circuit.

The risks of poor operation or of damage are then much reduced. However, arrangements are made to avoid blocking of the aspiration and return pipes by slurries or by particles. It is recommended that the jet pump and the adjacent parts to it, from the discharge and sampling arms, form a single detachable element of the circulation unit, and that the device additionally includes an unblocking assembly which replaces the circulation unit element and connects the driving arm to complementary parts of the aspiration and return arms in order to force water under pressure, at will, into the aspiration and return arms so as to unblock them.

The method can be carried out more easily with other improvements, which can be adopted separately or in combination : a screwing—unscrewing device, possibly automatic, capable of gripping the stoppers of the flasks, of turning them and removing them when they are detached ; a flask support including a lifting plate thanks to which the flasks can be pressed under the support plate ; and a mobile support such as an arm that turns to bring the flask, in turn to the screwing—unscrewing device and to the support plate.

BRIEF DESCRIPTION OF THE DRAWINGS

The invention will now be described in more detail with the help of the following illustrative figures which describe an embodiment of it.

DETAILED DESCRIPTION OF THE PREFERRED EMBODIMENTS

Figure 1:
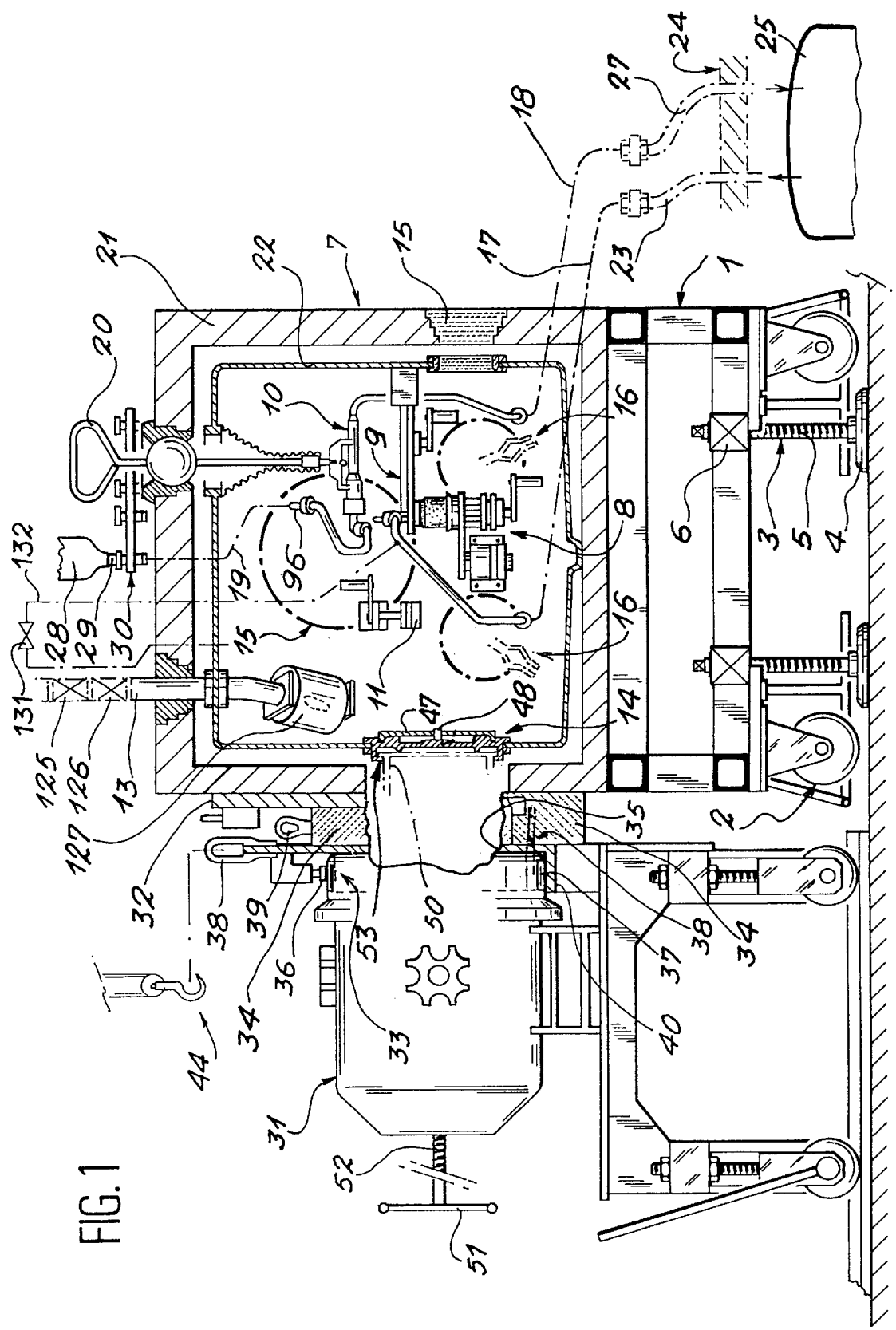
FIG. 1 is an overall view of the device.

As it can be seen in FIG. 1, the device of the invention is a vehicle mounted on a frame 1 fitted with wheels 2 which allow it to be moved to the product aspiration and return pipes 23 and 27 (in practice arranged in a line ; only one of each is shown), and with feet 3 that include a footing block 4 on the end of a threaded stem 5 that can be turned in a nut 6 integral with the frame 1 in order to set the footing block 4 on the ground and thereby stop the vehicle at the desired location for sampling by raising the wheels 2.

The frame 1 carries a protective enclosure 7 which is occupied, in particular, by a flask support 8, a support plate 9, a circulation unit 10, a screwing—unscrewing device 11 which will be made the subject of subsequent figures. There are also elements that pass through the enclosure 7, and in particular, an entry channel for the flasks 13, an opening 14 for the exit of the flasks, viewing ports 15, openings for the passage of tongs 16 which make it possible to work within the enclosure 7, a section of the return arm pipework 18 that connects the support plate 9 to the return pipe 27, a section of the driving arm pipework 19, and a pulling device 20 that supports the circulation unit 10, in order to raise the support plate 9 if one wishes ; and also the channels carrying electricity or fluid for control purposes which are not shown. The enclosure 7 is composed of an external, radiologically protective wall 21 which absorbs radiation and a box structure 22 that forms an internal liner and ensures the seal.

The entry channel 13 includes two valves 125 and 126 mounted in series, forming an airlock and which allow the safe and if desired stepped introduction of the flasks 67. It is terminated by a housing where the flasks can be grasped.

The exit opening 14 is designed so that one can place a shielded coffin 31 next to it, that is to say a movable, radiologically protective enclosure intended for the transport of the radioactive samples taken, to the analysis installation. The wall 21 is fitted with an enclosure port 32 that notably includes a sliding protective plate 34 that closes off the opening 14. A coffin port 33 of the same kind closes off the opening of the coffin 31. If the protective plate 34 is coupled to the coffin port 33 and if this assembly is removed by pulling on the lifting eyebolt 39, arranged at the top of the protective plate 34, the inside of the coffin is put into communication with the opening 14.

It then suffices to open a port 47 of the liner 22 so that the flasks full of samples can be transferred into the coffin 31.

The port in the liner 47 opens towards the inside of the liner 22, by pulling on a handle 48 via one of the tongs fitted in the liner 22.

The product aspiration and return pipes 23 and 27 end in tanks full of product to be sampled and analysed; these tanks 25 are situated under a biologically protective slab 24. As for the driving arm 19, it leads to a pressurized water system 28 via a supply pipe 29 which can be opened or closed by a valve 30 rigidly fixed to the enclosure 7.

Figure 2:
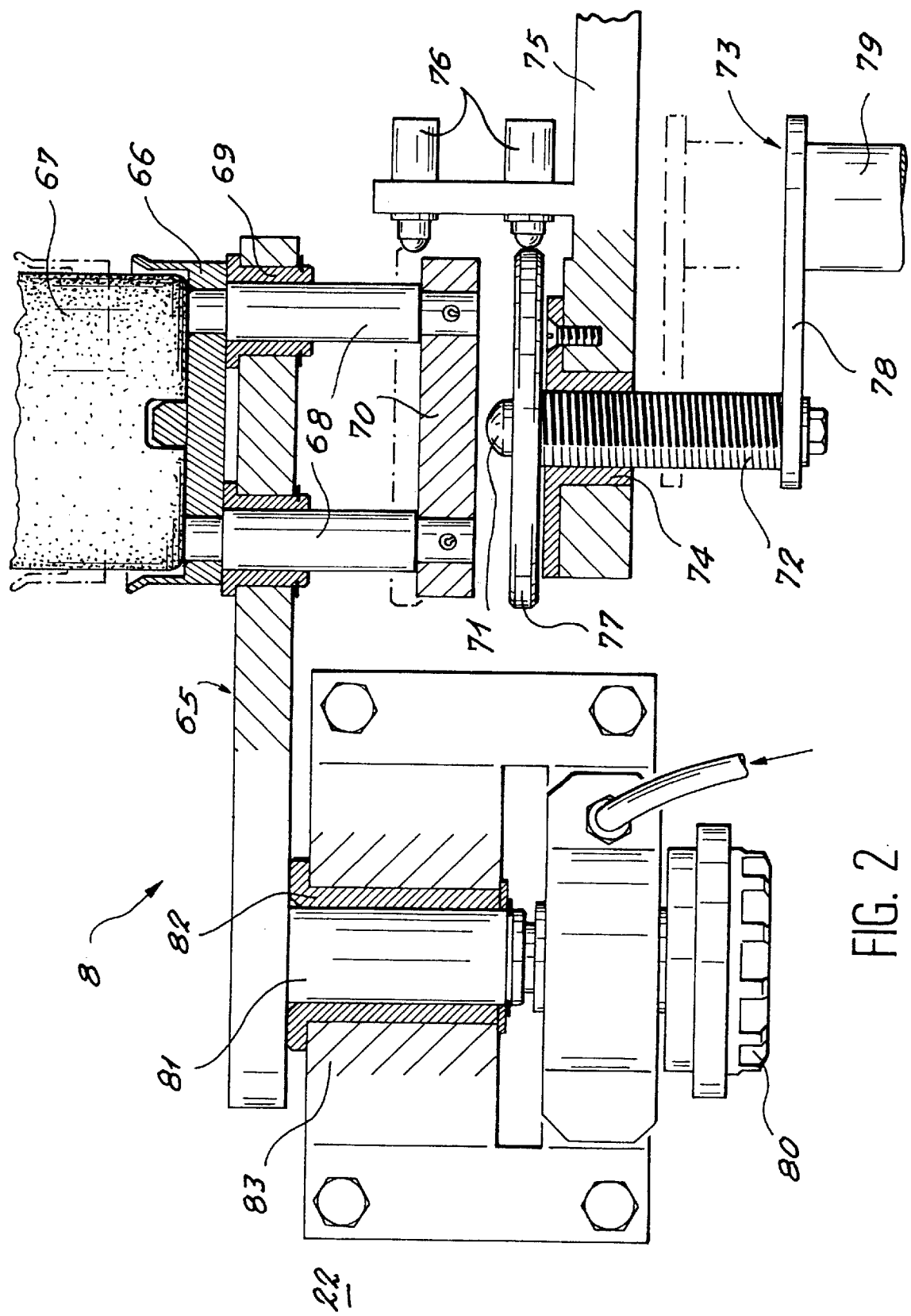
FIG. 2 is a view of the flask support.

The flask support 8 is illustrated in FIG. 2. Essentially it includes a rotating arm 65 and a lifting plate 66 on which a flask 67, called a pitcher from now on, in accordance with the term habitually used by the applicant, is placed. The lifting plate 66 is fixed to the top of two small pillars 68 which slide within guide rings 69 made through the rotating arm 65. The feet of the pillars 68 are joined to one another by a base 70 to which they are fixed and which hangs over a rounded top 71 of a threaded stem 72 whose lower end is rigidly fixed to a crank 73. The threaded stem 72 engages with a threaded sleeve 74 fixed to a bracket 75 which is itself fixed to the liner 22. By turning the crank 73, the threaded stem rises and consequently the base 70, the small pillars 68 and the lifting plate 66 also rise, as soon as the rounded top 71 comes into contact with the base 70. Two end of travel sensors 76 are fixed to the bracket 75, that work with a disc 77 rigidly fixed to the threaded stem 72 so as to check that the end conditions of vertical movement are achieved. Mechanical abutments are formed a little further on by the disc 77 and the lever 78 of the crank 73 against the ends of the threaded sleeve 74 housed in the bracket 75.

The vertical displacement of the pitchers 67 is provided by manual action on the handle 79 of the crank 73 by means of tongs 16.

The rotating arm 65 is turned by means of a rotating jack 80 which transmits movement to it through a vertical spindle 81 held in bearing 82 of a support structure 83 rigidly fixed to the liner 22.

Figure 3:
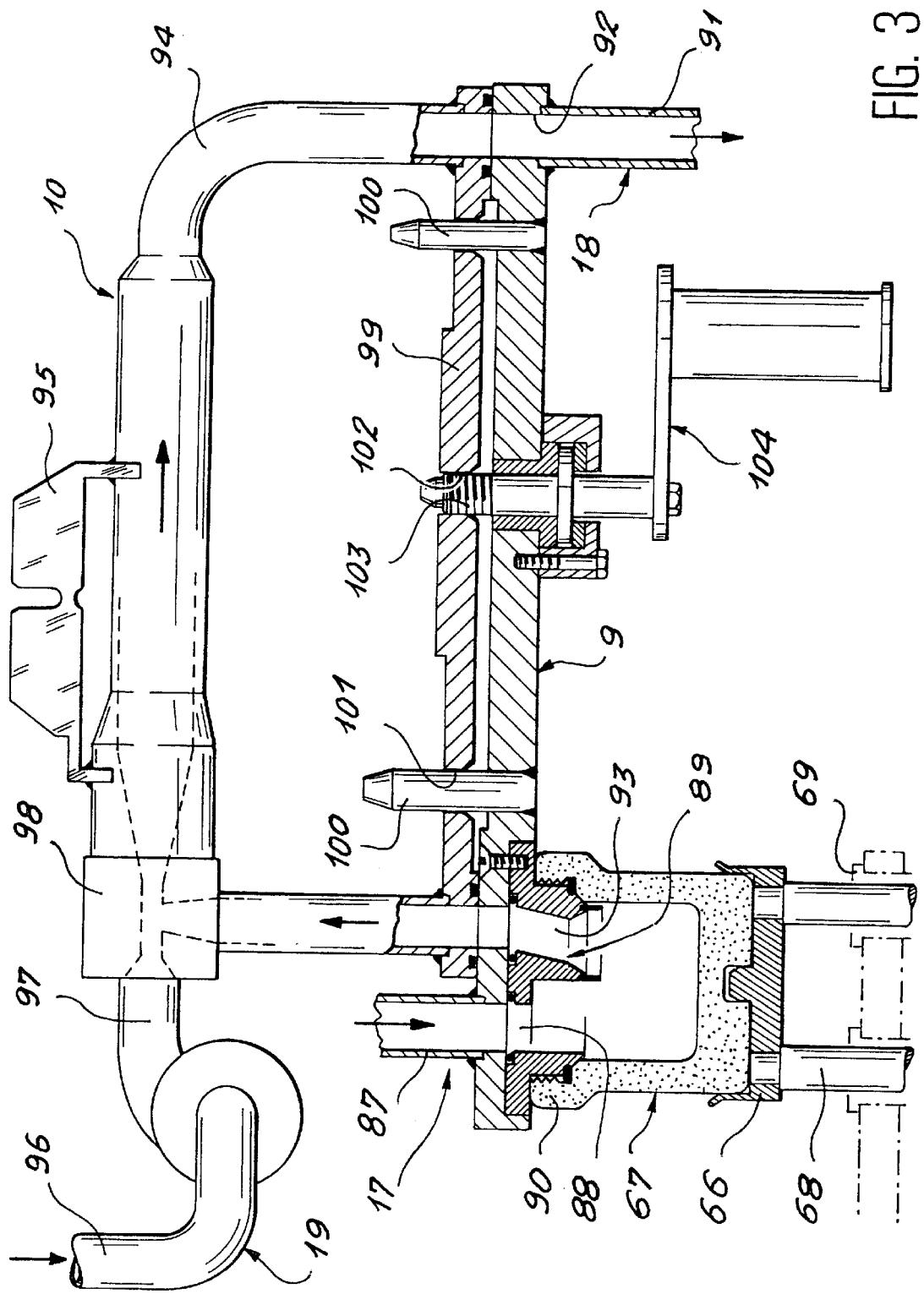
FIG. 3 is a view of the support plate and the circulation unit.

The pitcher 67 can be raised by the threaded stem 72 until it presses against the lower surface of the support plate 9 after having been brought underneath it. This is illustrated in FIG. 3.

The aspiration arm 17 includes a pipe 87 welded to the upper surface of the support plate 9 and which is extended through it to form an orifice 88 which emerges at the lower surface of a distribution collar 89 of the support plate 9 around which the rim 90 of the pitcher 67 fits. As for the return arm 18, it includes another pipe 91 welded to the lower surface of the support plate 9, well away from the distribution collar 89. Two orifices 92 and 93 pass through the support plate 9. Orifice 92 downstream from the circulation unit 10 extends the pipe 91 while orifice 93 upstream from the circulation unit 10 comes out at the lower surface of the distribution collar 89, at a level lower than orifice 88 and within the rim 90 of the flask 67, which therefore closes the liquid sampling circuit, whose aspiration and return arms are otherwise separated. The two orifices 92 and 93 are connected by an arch shaped pipe 94 of the circulation unit 10 in the middle of which a small plate has been welded which is used as a grip for the pulling device 20. As for the driving arm 19, it ends with a flexible part 96 connected to a branch 97 that is a part of the circulation unit 10 and which connects to the arch shaped pipe 94 extending it. The confluence is occupied by a Venturi 98 which forms the essential part of the circulation unit 10. By returning to FIG. 1, it can be seen that opening valve 30 causes water under pressure originating from the source 28 to flow and, having passed via the supply pipe 29 through the driving arm 19 and the Venturi 98 in order then to cause it to flow to a point downstream of the circulation unit 10 by passing the water notably through pipe 91 and the return pipe 27 to the tank 25 from which it originally came. This movement is accompanied by a pressure drop in the Venturi 98 under the effect of which the liquid to be sampled is aspirated from the tank 25 by a steady movement that avoids it being agitated or disturbed in any manner it rises within the aspiration arm 17, passes within pipe 87, into flask 67 and finally arrives at the Venturi 98, after which it blends in with the drive liquid and its surplus returns to the tank 25. The circulation unit 10 is therefore a jet pump with no rotating mechanical components or parts that move in any other way. When the valve 30 is closed again, product originating in the drum 25 remains in the pitcher 67 which can then be withdrawn from the support plate and stoppered using the screwing—unscrewing device 11.

The pipe 87 is vented by opening a venting valve 131 arranged on a vent pipe 132 connected to pipe 87 (FIG. 1) before stopping the flow of the drive water, which has the effect of stopping the aspiration of the contents of the tank 25. The venting valve 131 is fitted at the top of the vent pipe 132, outside the enclosure 7. However, the end of the vent pipe 132 returns into the enclosure 7 in order to avoid any risk of discharging contaminated product to the outside. The aspiration then causes pipe 87 to empty itself and the transfer of product continues by siphoning until the level of the liquid in flask 67 has gone down below the rim of orifice 93 (lower than that of orifice 88) ; the drive water is then turned off, and the siphoning continues within the circulation unit 10 until it is empty. The pitcher 67 remains close to full of sampled product while no liquid residue from the circulation unit 10 will disturb it by running into it.

The circulation unit 10 also includes a cross-slide below it and positioned on the support plate 9. The correct setting of the circulation unit 10 is ensured by two pins 100 which pass through holes 101 in the cross-slide 99. The ends of the arch shaped pipe 94 then extend the orifices 92 and 93 and furthermore a threaded stem 102 suspended from the support plate 9 is in front of a tapped hole 103 that passes through the cross-slide 99. It then suffices to turn a crank 104 which causes the threaded stem to engage in the tapped hole 103 and ensures the cross-slide 99 is locked and therefore provides the seal for the connections of the parts of the aspiration arm 17 and the parts of the return arm 18 and holds the circulation unit 10 in place.

Figure 4:
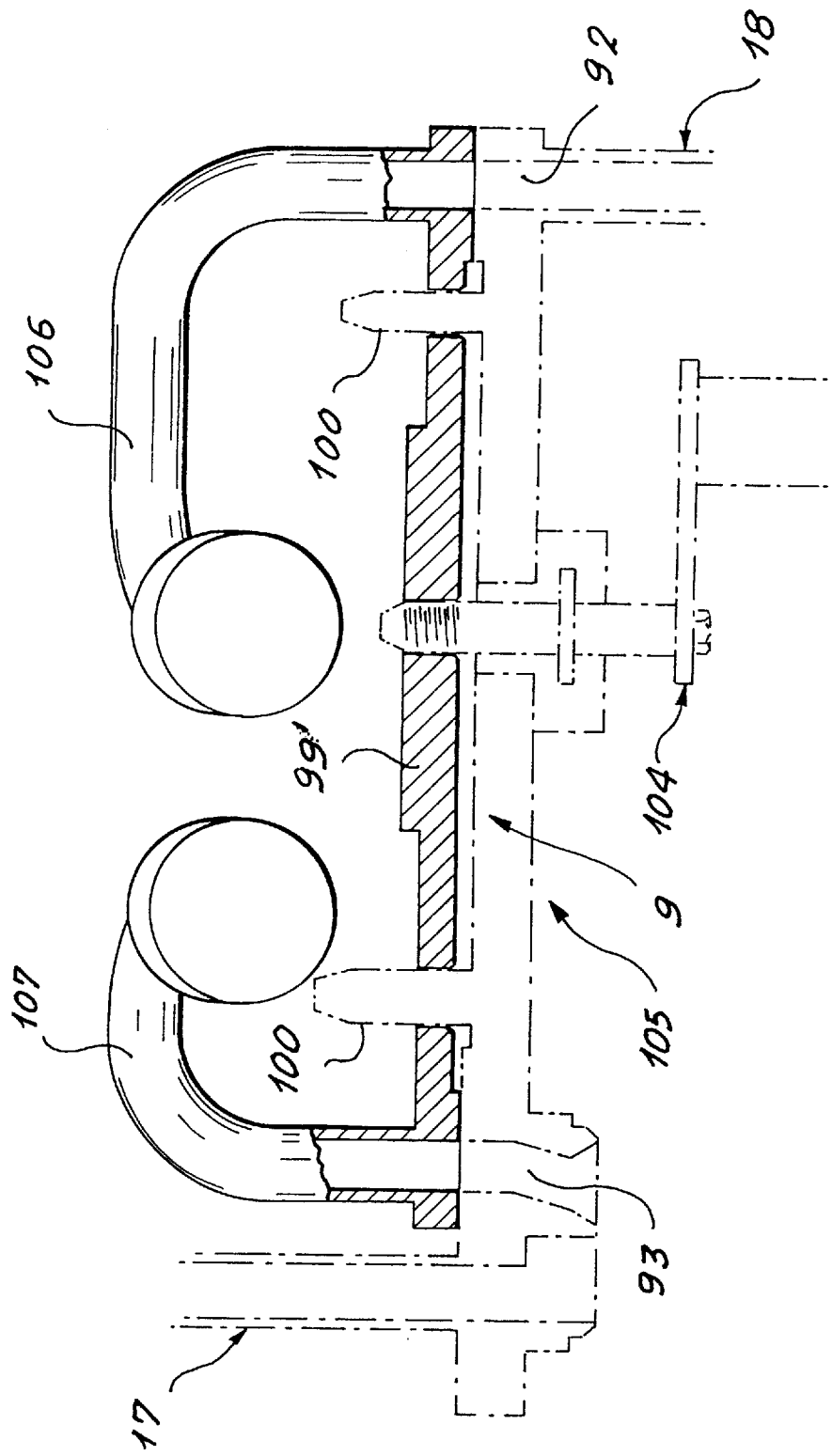
FIG. 4 is a view of the connection assembly intended to unblock the pipes.

The circulation unit 10 can be replaced, after having been removed by the pulling device 20, by a dummy bar 105 shown in FIG. 4 and which includes, besides a cross-slide exactly similar to the cross-slide 99 of the circulation unit 10 and which therefore carries the reference number 99', so that no further description is judged necessary, connecting sections 106 and 107 for unblocking and which will form a continuation of orifices 92 and 93 when the dummy bar is assembled. By connecting the end of the flexible part 96 of the drive arm 19 to the free ends of these connecting sections 106 and 107, one can cause water under pressure to gush into the upstream part of the return arm 18 and, with counterflow of the flow of the liquid sampled from the tank 25, into the aspiration arm 17 through the pitcher 67. It would then be possible to unblock these sections of the piping system if they were blocked by an accumulation of particles. Otherwise the dummy bar 105 is not used but is disassembled from the support plate 9 and stored somewhere within the liner 22.

Figure 5:
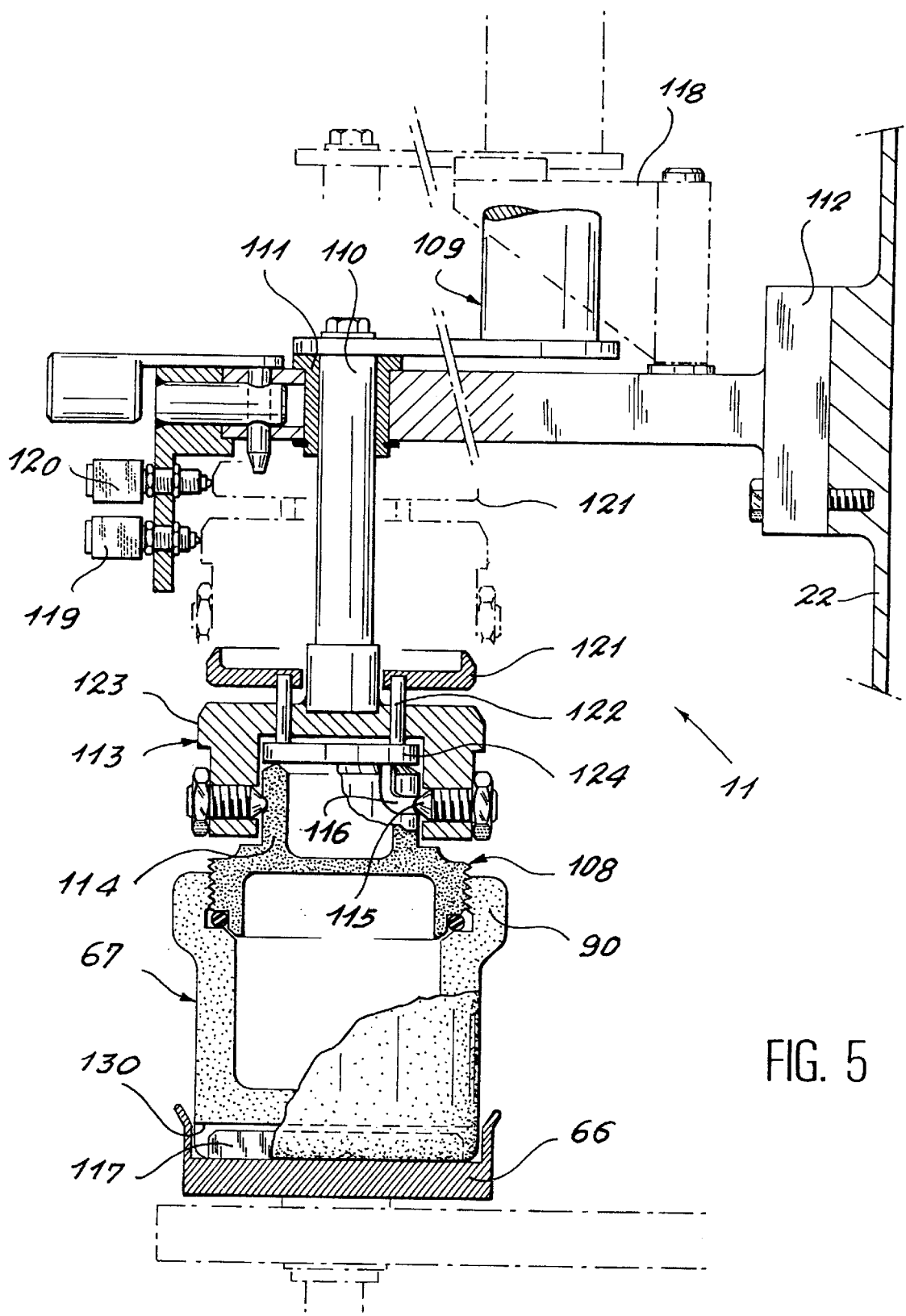
FIG. 5 is a view of the screwing - unscrewing device.

We pass now to the device for screwing and unscrewing, illustrated completely in FIG. 5.

The pitchers 67 carry a stopper 108 screwed to their rim 90. The drive element for the screwing—unscrewing device is again a crank 109 which causes rotation of a spindle 110 carried in a bush 111 of a support structure 112 fixed to the liner 22. At its lower end, the spindle 110 carries a hollowed out mandrel 113 which fits over a nipple 114 at the top of the stopper 108. The mandrel 113 is equipped with projections 115 on its internal surface which can go into bayonet fitting slots 116 in the sleeve 114. In order to grip the stopper 108 of a pitcher 67 which has recently been brought under the screwing—unscrewing device 11, the handle of the crank 109 is lifted—which is possible because of the ability of the spindle 110 to slide within the bush 111—then it is allowed to fall whilst turning it so that the internal projections 115 go into the bayonet fitting slots 116. When they arrive at the end of these slots, continuation of the movement of the crank 109 causes movement of the stopper 108 and unscrews it. For this purpose, the bottom of the pitcher is slotted with a rectilinear slot 130 into which fits a tenon 117 made diametrically on the seat of the lifting plate 66 and which checks the rotation of the body of the pitcher 67. When the unscrewing is finished, the crank 109 is entirely raised again and placed on a bracket 118 of the support structure 112 until the pitcher 67 full after having been brought under the circulation unit 10 and then brought back, must be closed again, this being carried out by a reverse operation of the crank 109. One will also note two sensors 119 and 120 fixed to the support structure 112, the first of which detects the presence of the mandrel 113 when this is completely raised again, whilst the second, situated a little above the first, detects the presence of a disc 121 supported by small pillars 122 which slide through cover 123 of the mandrel 113 and which are joined by a ring 124 which extends under this cover 123. When no stopper 108 has been gripped by the mandrel 113, the disc 121 rests on the cover 123 and the ring 124 is suspended from it. When, contrary to this a stopper 108 is held by the internal projections 115, its nipple 114 raises the ring 124 and the disc 121, which allows the latter to reach the height of the second sensor 120 and to be marked by it when the crank 109 is completely raised again and that the mandrel 113 is arriving at the height of the first sensor 119. A more certain operation is thereby obtained.

When the desired samples have been taken, the full pitchers 67 can be picked up by one of the tongs and put into the coffin 31.

We claim:

1. A device for taking samples of noxious liquids charged with solid particles from a tank (25) and depositing said samples into a flask having a rim, said device comprising:

a sampling circuit that includes a vent, an aspiration pipe leading to the tank (25) and a return pipe, said aspiration pipe and said return pipe each having an end;

a unit (10) for circulating liquid through the sampling circuit; and a support plate (9) under which the ends (88, 93) of the aspiration and return pipes are disposed, the rim (90) of the flask being applied under the support plate around said ends; and wherein the aspiration and return pipes are without communication other than via the flask applied under the support plate, the liquid circulation unit (10) is situated in the return pipe and the aspiration pipe is connected to the vent (131, 132).

2. A device for taking samples of noxious liquids according to claim 1, wherein an external aspiration pipe and an external return pipe extend into the tank, and wherein the device further comprises:

an enclosure (7) equipped with access means (13, 14) for entry and exit of the flask, the return and aspiration pipes and the support plate being situated within the enclosure, the aspiration and return pipes being connected to the external aspiration (23) and return (27) pipes outside the enclosure (7); and application means (8, 11, 16) disposed in the enclosure for gripping the flask, removing the flask and putting a stopper in the flask and for applying the rim (90) of the flask under the support plate; and wherein the vent (131, 132) includes a pipe (132) having an end disposed within the enclosure (7) and having a portion disposed outside the enclosure and fitted with a venting valve (131).

3. A device for taking samples of noxious liquids according to claim 2, wherein the application means includes a flask support (67) that includes a lifter plate (66).

4. A device for taking samples of noxious liquids according to claim 3, wherein the application means further comprises a mechanical screwing and unscrewing apparatus that has a head (113) capable of gripping the stopper and turning the stopper and lifting the stopper from the flask.

5. A device for taking samples of noxious liquids according to claim 4, wherein the application means further comprises a movable support (65) that carries the lifter plate in order to selectively position the lifter plate under one of the support plate (9) and the screwing and unscrewing apparatus (11), said lifter plate including an element (117) to stop the rotation of the flask.

6. A device for taking samples of noxious liquids according to claim 4, wherein the screwing and unscrewing apparatus further comprises:

a control crank (109) for the head (113), the control crank having a sliding axis of rotation (110);

and a support bracket (118) for the crank (109) at a position remote from the flask.

7. A device for taking samples of noxious liquids according to claim 3, wherein the application means further comprises a cranking device (79) for controlling the lifter plate.

8. A device for taking samples of noxious liquids according to claim 2, further comprising a movable container; and wherein the access means through the enclosure include a flask introduction passageway and a connecting port to the movable container (31).

9. A device for taking samples of noxious liquids according to claim 2, wherein the device is movable, the enclosure being mounted on wheels (2).

10. A device for taking samples of noxious liquids according to claim 1, wherein the circulation unit (10) includes a jet pump (97, 98) and the sampling circuit includes a driving pipe supplied with liquid under pressure, said driving pipe supplying the pressurized liquid to the circulation unit.

11. A device for taking samples of noxious liquids according to claim 10, wherein the jet pump (97, 98) and adjacent parts (94) of the return and aspiration pipes form a single and detachable element of the circulation unit; and wherein the single and detachable element of the circulation unit and the support plate are fitted with mutual fixing means and means for connecting complementary parts of the aspiration arm and the return arm (99 to 104) fixed to the support plate (9) and the circulation unit element (10).

12. A device for taking samples of noxious liquids according to claim 11, wherein the single and detachable element of the circulation unit includes a cross slide (99) positioned on a top face of the support plate (9) and assembled in a detachable way on the support plate.

13. A device for taking samples of noxious liquids according to claim 12, further comprising: a backblowing assembly (105) having two pipes (106, 107), each with first and second ends, and means (99') for fixing the backblowing assembly to the support plate (9) and for connecting the first ends of the pipes to the aspiration pipe and the return pipe and the second ends of the pipes to the driving pipe.

14. A device for taking samples of noxious liquids according to claim 13, wherein the pipes (106, 107) are separated and the driving arm has a flexible part (96).

15. A device for taking samples of noxious liquids according to claim 13, wherein the backblowing assembly includes a cross slide (99') identical to the cross slide (99) of the single and detachable element of the circulation unit.

16. A device for taking samples of noxious liquids according to claim 1, wherein the return line is for connection to the tank.

* * * * *